United States Patent [19]

Wakamatsu et al.

[11] Patent Number: 5,514,518
[45] Date of Patent: May 7, 1996

[54] METHOD OF IMPROVING DELAMINATION IN AN IMAGE FORMING MATERIAL UTILIZING 2-DIAZO-1,2-QUINONE COMPOUNDS HAVING FLUORINE CONTAINING SUBSTITUENT GROUPS

[75] Inventors: Kan Wakamatsu; Yuichi Wakata; Masato Satomura; Tomizo Namiki, all of Shizuoka, Japan

[73] Assignee: Fuji Photo Film Co., Ltd., Kanagawa, Japan

[21] Appl. No.: 315,574

[22] Filed: Sep. 30, 1994

Related U.S. Application Data

[62] Division of Ser. No. 93,722, Jul. 20, 1993, Pat. No. 5,384,227, which is a division of Ser. No. 736,343, Jul. 26, 1991, Pat. No. 5,312,905.

[30] Foreign Application Priority Data

Jul. 27, 1990 [JP] Japan ..................................... 2-200989
Dec. 1, 1990 [JP] Japan ..................................... 2-400059

[51] Int. Cl.$^6$ ...................................................... G03F 7/34
[52] U.S. Cl. ........................... 430/253; 430/166; 430/328
[58] Field of Search .................................... 430/191, 253, 430/192, 325, 193, 326, 329, 166, 328; 534/556, 557

[56] References Cited

U.S. PATENT DOCUMENTS

| | | | |
|---|---|---|---|
| 3,711,285 | 1/1973 | Deutsch et al. | 534/557 |
| 4,839,256 | 6/1989 | Muller | 430/192 |

FOREIGN PATENT DOCUMENTS

| | | | |
|---|---|---|---|
| 1-167778 | 1/1986 | European Pat. Off. | 430/192 |
| 1331286 | 9/1973 | United Kingdom | 534/557 |
| 2038801 | 7/1980 | United Kingdom | 534/557 |

*Primary Examiner*—Charles L. Bowers, Jr.
*Assistant Examiner*—Christopher G. Young
*Attorney, Agent, or Firm*—Sughrue, Mion, Zinn, Macpeak & Seas

[57] ABSTRACT

A 2-diazo-1,2-quinone compound having a substituent group containing an alkyl group which is substituted by at least one fluorine atom is described. This compound has a capacity to change its polarity when exposed to light. The invention also provides an image forming material in which the invention compound is added to at least one of laminated layers. When these laminated layers are exposed to light, the adhesiveness of the compound-containing layer to its adjoining layer is reduced effectively due to the polarity-changing ability of the compound, thus making the easy delamination of the layers possible. This compound is applicable to many instances in which image receiving sheets are used, such as the formation of a multi-color image by a transfer method (a color proof, for example) and the preparation of a printing plate of the delamination development type.

1 Claim, No Drawings

METHOD OF IMPROVING DELAMINATION IN AN IMAGE FORMING MATERIAL UTILIZING 2-DIAZO-1,2-QUINONE COMPOUNDS HAVING FLUORINE CONTAINING SUBSTITUENT GROUPS

This is a divisional of application No. 08/093,722 filed Jul. 20, 1993, U.S. Pat. No. 5,384,227 which is a divisional of application No. 07/736,343 filed Jul. 26, 1991, U.S. Pat. No. 5,312,905.

FIELD OF THE INVENTION

This invention relates to novel 2-diazo-1,2-quinone compounds which are capable of changing polarity when exposed to light. It also relates to image forming materials prepared by making use of these compounds, which are applicable to recording materials such as color proof image receiving sheets, photoresists, printing plates, PS plates, and the like.

BACKGROUND OF THE INVENTION

In the case of a multiple layer recording material, it is preferable to prepare the material in such a manner that the adhesive strength between its layers can be controlled. Even in the case of a monolayer recording material, it may be convenient for many purposes if the material is prepared in such a manner that the adhesive strength between its supporting body and the monolayer can be controlled.

For example, a means for reducing the adhesive strength between layers making use of the effect of light has been disclosed in European Patent 0,156,535, in which a surfactant is formed when the layers are exposed to light. Also, a delamination development method has been disclosed in *Photographic Science and Engineering*, Vol. 22, No. 3, pp. 138–141 (1977), in which delamination is effected by the formation of gas from a diazo compound or an azide compound when the compound is exposed to light. Neither of them, however, seems to have satisfactory effect.

When a 2-diazo-1,2-quinone compound is exposed to light, it is converted into nitrogen gas and an indene carboxylic acid derivative induced by Wolff rearrangement. Recording materials prepared by making use of such an optical rearrangement reaction, especially positive type sensitive compositions, have been disclosed, for example, in U.S. Pat. No. 3,046,110, U.S. Pat. No. 3,046,111, U.S. Pat. No. 3,046,123, U.S. Pat. No. 3,046,124, U.S. Pat. No. 3,106,465, U.S. Pat. No. 3,130,047, and JP-B-46-21247 (corresponding to U.S. Pat. No. 3,640,992) (the term "JP-B" as used herein means an "examined Japanese patent publication"). However, there are no reports on the application of the optical rearrangement reaction to a process for the reduction of adhesive strength between layers with the aid of exposure to light.

Also, changes in the adhesive strength between a layer and a base board caused by the photolysis of these diazo compounds have been applied to dry type image formation processes. For example, an image forming process has been disclosed in JP-A-52-57819 (the term "JP-A" as used herein means an "unexamined published Japanese patent application"). According to this process, a transparent plastic film coated with a layer of a sensitive composition comprising a diazonium salt and a binder is superposed on a supporting sheet coated with an adhesive layer to prepare a laminate. When the thus prepared laminate is exposed to light and then the plastic film is delaminated from the supporting sheet, the unexposed portion of the sensitive composition layer remains on the transparent plastic sheet while the exposed portion remains on the supporting sheet.

In addition, processes for the formation of relief images have been disclosed, for example, in JP-A-54-79032, JP-A-54-79033 and JP-A-54-79034 (corresponding to U.S. Pat. Nos. 4,210,711, 4,334,006 and 4,396,700). According to these processes, an imagewise forming material comprising a sensitive composition is superposed on a supporting sheet which is noncohesive at ordinary temperatures, and the thus prepared laminate is subjected to imagewise exposure and then heated at a temperature higher than the softening point of the sensitive composition. Thereafter, the recording material is delaminated from the supporting sheet at a temperature which is lower than the heating temperature. In this way, the exposed image portion of the sensitive composition layer is selectively adhered to the supporting sheet to form a relief image.

However, because of an insufficient difference between the adhesive strength of the exposed and unexposed portions, none of these dry type processes can produce satisfactory images.

An image receiving sheet which comprises two image receiving layers of organic polymer materials superposed on a support has been disclosed in JP-A-61-189535 (corresponding to U.S. Pat. No. 4,766,053), in which the delamination strengths between the two image receiving layers and between the second image receiving layer and an image layer can be controlled in such a manner that the image layer can be transferred onto a permanent support not only singly but also together with the second image receiving layer at will. This image receiving sheet has an advantage in that optical gain of an image can be controlled by either introducing or not introducing a step for the transfer of the second image receiving layer and by changing the thickness of the second image receiving layer to be transferred. In addition, because of the thickness of the image receiving layer being thin on the image layer, the image receiving layer can reproduce the irregularity of the surface of the permanent support more accurately to give a natural matting effect. This image receiving sheet, therefore, can be used suitably for the preparation of a color proof having excellent print approximation.

This process, however, has the following problems with regard to the setting condition of the adhesiveness between the first and second image receiving layers.

1) The adhesiveness between the first and second image receiving layers should be strong when an image is transferred to the image receiving sheet (if the adhesiveness is too weak, delamination will occur between the first and second image receiving layers when the image support is delaminated).

2) The adhesiveness between the first and second image receiving layers should be weak when an image layer is transferred to a permanent support (if the adhesiveness is too strong, picking will occur when the image receiving sheet support is delaminated).

SUMMARY OF THE INVENTION

In view of the above, it is therefore an object of the present invention to provide a novel compound which, when added to at least one layer of a multiple layer recording material or to the layer of a monolayer recording material, can weaken the adhesiveness between the layers in a multiple layer recording material or between the monolayer and the other material in a monolayer recording material by the effect of the exposure to light. This invention also provides an image forming material in a monolayer recording material prepared by making use of the novel compound. Another principal object of the present invention is to provide a novel compound which can weaken the adhesiveness of the surface of a coating layer by localizing on the surface.

Particularly, the present invention provides a 2-diazo-1,2-quinone compound having a substituent group containing an alkyl group which is substituted by at least one fluorine atom. Preferably, the 2-diazo-1,2-quinone compound is a 2-diazo-1,2-naphthoquinone compound wherein the 4- or the 5-position of the compound is substituted by the substituent group containing an alkyl group which is substituted by at least one fluorine atom. Also, the 2-diazo-1,2-quinone compound preferably is a 2-diazo-1,2-naphthoquinone compound wherein the alkyl group which is substituted by at least one fluorine atom is bound to the 2-diazo-1,2-naphthoquinone group through a sulfonate or an amide.

Also, the present invention provides an image forming material which comprises a layer superposed on a support, wherein the layer contains a 2-diazo-1,2-quinone compound having a substituent group containing an alkyl group which is substituted by at least one fluorine atom.

Other objects and advantages of the present invention will be apparent as from description below.

DETAILED DESCRIPTION OF THE INVENTION

In order to overcome the aforementioned problems involved in the art, the inventors of the present invention have conducted intensive studies and found that 2-diazo-1,2-quinone compounds, especially a new compound developed by the inventors, can exhibit a suitable function for use in a process in which the adhesiveness between layers is weakened by means of light exposure. That is, the objects of the present invention were achieved by the development of a novel 2-diazo-1,2-quinone compound having a substituent group containing an alkyl group which is substituted by at least one fluorine atom and by the development of an image forming material having a layer containing the novel compound.

The 2-diazo-1,2-quinone compound according to the present invention include compounds which are represented by the following formula (I):

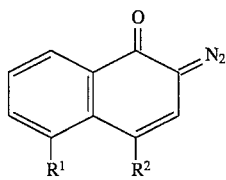 (I)

wherein one of $R^1$ and $R^2$ is a hydrogen atom and the other is a substituent group containing an alkyl group which is substituted by at least one fluorine atom.

Suitable examples of the substituent group containing an alkyl group which is substituted by at least one fluorine atom include groups that are represented by the following formula (II) or (III):

wherein $R^3$ and at least one of $R^4$ and $R^5$ represent a substituent group containing an alkyl group which has 2 to 20 carbon atoms and is substituted by at least 3 fluorine atoms.

Illustrative examples of the substituent group containing an alkyl group which has 2 to 20 carbon atoms and is substituted by at least 3 fluorine atoms include alkyl groups which are substituted by fluorine atoms, such as 2,2,2-trifluoroethyl, 3,3,3,-trifluoropropyl, 1,1,1,3,3,3,-hexafluoro-2-propyl, 1H,1H-pentafluoropropyl, 1H,1H-heptafluorobutyl, 1H,1H-nonafluoropentyl, 1H,1H-undecafluorohexyl, 1H,1H,2H,2H-pentafluoro-1-butyl, 1H,1H,2H,2H-nonafluoro-1-hexyl, 1H,1H,2H,2H-tridecafluoro-1-octyl, 1H,1H,2H,2H-heptadecafluoro-1-decyl, 1H,1H,2H,2H-henicosafluoro-1-dodecyl, 1H,1H,5H-octafluoropentyl, 1H,1H,7H-dodecafluoroheptyl, 1H,1H,9H-hexadecafluorononyl, 1H,3H,3H-tetrafluoropropyl, 1H,5H,5H-octafluoropentyl, 1H,7H,7H-dodecafluoroheptyl, 1H,9H,9H-hexadecafluorononyl, 1H,11H,11H-eicosafluoroundecyl, perfluoroalkylmethyl, perfluoroalkylethyl (wherein perfluoroalkyl is represented by the formula $C_nF_{2n+1}$, n=2 to 18) groups, and the like, and phenyl groups containing an alkyl group which is substituted by fluorine atoms, such as perfluoroalkylmethylphenyl, perfluoroalkylethylphenyl, perfluoroalkylmethoxyphenyl, perfluoroalkylethoxyphenyl, (perfluoroalkylmethylthio) phenyl, (perfluoroalkylethylthio) phenyl, perfluoroalkylmethylsulfonylphenyl, perfluoroalkylethylsulfonylphenyl,perfluoroalkylmethoxycarbonylphenyl, perfluoroalkylethoxycarbonylphenyl groups, and the like.

A particularly preferred compound among the compounds represented by formula (I) may have a structure in which the 2-diazo-1,2-naphthoquinone group is substituted by a sulfonate group containing an alkyl group, most preferably at the 4-position. In this instance, the alkyl group contained in the sulfonate group may have 2 to 20 carbon atoms, preferably 4 to 15 carbon atoms, and at least half the number of hydrogen atoms in the alkyl group are substituted by fluorine atoms.

The following describes a process for the synthesis of the compound represented by formula (I).

The compound represented by formula (I) can be obtained by the condensation reaction of a compound containing a hydroxy group or an amino group and also containing an alkyl group which is substituted by fluorine atoms, as represented by the following formula (IV) or (V), with a 2-diazo-1,2-naphthoquinonesulfonyl chloride compound represented by the following formula (VI), in the presence of a deoxidizer:

wherein $R^3$, $R^4$ and $R^5$ have the same meaning as described above, and

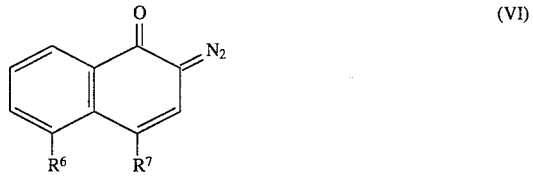

wherein one of $R^6$ and $R^7$ is a hydrogen atom and the other is a group represented by —SO$_2$—Cl.

Suitable examples of the compound represented by the formula (VI) include 2-diazo-1,2-naphthoquinone-4-sulfonyl chloride and 2-diazo-1,2-naphthoquinone-5-sulfonyl chloride.

The solvent for use in the condensation reaction may be selected from various organic solvents, but preferably it is selected from diethyl ether, acetone, dichloromethane, chloroform, carbon tetrachloride, tetrahydrofuran, dioxane, benzene, toluene, acetonitrile, and the like. The deoxidizer may be selected from various organic amines, but preferably it is selected from pyridine, diethylamine, triethylamine, N,N-dimethylaniline, N,N-diethylaniline, and the like. The condensation reaction may be carried out preferably using 1 mole equivalent of the compound represented by formula (IV) or (V), 1 to about 1.2 moles equivalent of the compound of formula (VI), and 1 to about 1.2 moles equivalent of the deoxidizer, at a preferred reaction temperature of about from −10° C. to 40° C.

Similar to the case of commonly known 2-diazo-1,2-quinone compounds, the 2-diazo-1,2-quinone compound of the present invention undergoes Wolff rearrangement when exposed to light and subsequently forms nitrogen gas and a carboxylic acid compound. When the 2-diazo-1,2-quinone compound of the present invention is added to at least one layer of a multiple layer recording material and the resulting material is exposed to light, the compound changes its polarity due to the optical rearrangement reaction described above and, as the result, effectively reduces the adhesion strength between the compound containing layer and its adjoining layer. Consequently, if it is necessary to have a step for a strong adhesiveness between these two layers and another step for a weak adhesiveness among a series of steps of an image forming process using the just-described multiple layer recording material, such a different adhesion strength required for each of the two steps can be realized by adding the 2-diazo-1,2-quinone compound of the present invention to at least one of these two layers and by further interposing a light exposure step between these two steps (e.g., a light of an ultra-high pressure murcury lump (1 kw) at a distance of 90 cm for 15 seconds or longer).

In consequence, it is possible to apply the 2-diazo-1,2-quinone compound of the present invention effectively to image forming materials which forms visible difference between exposed portion and unexposed portion such as a color proof image receiving sheets and a photoresist, a printing plate, and the like based on the delamination development.

The 2-diazo-1,2-quinone compound of the present invention is contained in a layer with being localized on the surface thereof whereas known compounds are uniformly present in the layer. Therefore, the use of the compound of the present invention effectively results in reduction of adhesion strength.

The following describes an example of the application of the 2-diazo-1,2-quinone compound of the present invention to an image receiving sheet for color proof use.

Though not specifically limited, a support for use in an image receiving sheet may be selected from chemically and thermally stable materials such as a polyethylene terephthalate film, a polycarbonate film and, as occasion calls, a sheet of paper laminated with a polyethylene film. In order to improve the adhesion strength of the support to a first image receiving layer, the support may be subjected to a surface treatment such as corona discharge or glow discharge, or may be superposed with an undercoat layer. The undercoat layer may be effected by any means, provided that it can improve the adhesion strength between the support and the first image receiving layer, but preferably it is effected by silan coupling.

The organic polymer material to be used in the first layer may be selected preferably from those materials having a softening point of about 80° C. or lower as determined by the Vicat test, more precisely, in accordance with the standard method for the measurement of the softening point of polymers, ASTM D 1235, established by American Society for Testing Materials. An advantage of using such a low softening point organic polymer material is that, when a transferable image which has been transferred to an image receiving sheet material is re-transferred to a permanent support such as paper by heat and pressure, the image receiving layer is adhered effectively to the permanent support in proportion to the irregularity of the surface of the support. The use of such a polymer material also improves print approximation because the steps for matting and the like can be omitted at the time of delamination. On the contrary, if a polymer material having a high softening point is used, not only is a high temperature required for the transfer step, but also the dimensional stability of an image and like properties will be spoiled. Consequently, when a polyethylene terephthalate film or the like is used as a support of a sensitive material or an image receiving material, the organic polymer material to be laminated may have a softening point of about 80° C. or lower as determined by the Vicat test, preferably 60° C. or lower, more preferably 50° C. or lower.

At least one compound selected from the group consisting of the following illustrative examples may be used as the polymer material having a softening point of about 80° C. or lower: polyolefins such as polyethylene, polypropylene and the like, ethylene copolymers such as a copolymer of ethylene and vinyl acetate, a copolymer of ethylene and an acrylic ester and the like, polyvinyl chloride, vinyl chloride copolymers such as a copolymer of vinyl chloride and vinyl acetate and the like, polyvinylidene chloride, vinylidene chloride copolymers, polystyrene, styrene copolymers such as a copolymer of styrene and (meth)acrylate and the like, polyvinyltoluene, vinyltoluene copolymers such as a copolymer of vinyltoluene and (meth)acrylate and the like, poly(meth)acrylate, (meth)acrylate copolymers such as a copolymer of butyl(meth)acrylate and vinyl acetate and the like, vinyl acetate, polyamide resins such as nylon, copolymerized nylon, N-alkoxymethyl nylon and the like, synthetic rubber, and chlorinated rubber. Other useful organic polymer materials having a softening point of about 80° C. or lower are disclosed, for example, in "Handbook of Plastics properties" (edited by Japan Plastics Molding Industries Association, Japan Federation of Plastics Industries; published by Kogyo-Chosa-Kai; Oct. 25, 1968).

The softening points of these organic polymer materials may substantially be lowered by adding a plasticizer which is compatible with these polymers. Even in the case of an organic polymer material having a softening point of more than 80° C., it is possible to lower the softening point substantially to a level of 80° C. or less by the addition of a compatible plasticizer. In order to control the adhesion strength of the first image receiving layer to its support or to a second organic polymer layer to be superposed on the first layer, these organic polymer materials may be further mixed with various types of other polymers, adhesion improvers, surfactants, lubricants, and the like, provided that the softening point does not exceed 80° C. by the use of these additives.

The first organic polymer layer may preferably have a thickness of from 1 to 50 μm, more preferably from 5 to 30 μm. One reason for such a limitation is that when an image which has been transferred to an image receiving sheet material is re-transferred to a permanent support, the layer should have a thickness which is greater than the irregularity depth of the surface of the support. Another reason is that when a transferable image which has different irregularity depths between its line and non-line portions is transferred to an image receiving sheet material, the first layer may be used as a thin film in the case of a monocolor system, but, in the case of a combination of four colors for use such as a color proof, it is preferable to make the first layer into a film which is four times thicker than the irregularity depth of the line and non-line portions of each color. A thickness of the first layer which is too great would result in failure in absorbing the irregularity depth of the surface of the support and nonuniform separation. On the other hand, the first layer being too thin would require extra step for drying.

The following describes a second image receiving layer which is superposed on the first layer. An object of the use of this second organic polymer layer is to re-transfer an image which has been transferred to an image receiving sheet to a permanent support together with only the thin second layer film by delaminating a support of the image receiving sheet together with its first image receiving layer, so that the irregularity of the surface of the permanent support remains unchanged and, therefore, an image close to the gloss of the actual print material can be obtained without requiring any special matting treatment. In consequence, any organic polymer material is applicable to the second image receiving layer, provided that it satisfies the adhesiveness relationships disclosed in U.S. Pat. No. 4,766,053. However, such an organic polymer material may preferably be selected from polymer materials having 10° C. or higher softening points than that of the first image receiving layer, depending on the organic polymer material used in the first layer, the image forming material used in the formation of a transferable image, and the permanent support material. In this instance, examples of the permanent support include art paper, coated paper, wood free paper, woody paper, metal sheets, synthetic films, and the like.

At least one compound selected from the group consisting of the following illustrative examples may be used as the polymer material of the second image receiving layer: polyolefins such as polyethylene, polypropylene and the like, ethylene copolymers such as a copolymer of ethylene and vinyl acetate, a copolymer of ethylene and an acrylic ester and the like, polyvinyl chloride, vinyl chloride copolymers such as a copolymer of vinyl chloride and vinyl acetate and the like, polyvinylidene chloride, vinylidene chloride copolymers, polystyrene, styrene copolymers such as a copolymer of styrene and (meth)acrylate and the like, polyvinyltoluene, vinyltoluene copolymers such as a copolymer of vinyltoluene and (meth)acrylate and the like, poly(meth)acrylate, (meth)acrylate copolymers such as a copolymer of butyl (meth)acrylate and vinyl acetate and the like, vinyl acetate, polyamide resins such as a nylon, copolymerized nylon, N-alkoxymethyl nylon and the like, synthetic rubber, chlorinated rubber, and cellulose compounds.

As an effective means to control physical film properties of the second image receiving layer such as stickiness, thermal adhesiveness, shelf life of the finally obtained image (adhesion resistance), and the like, a photopolymerizable monomer may be added to the second layer so that the second layer can be cured by its exposure to light after the re-transfer of an image to a permanent support.

The thickness of the second image receiving layer may preferably be in the range of from 0.1 to 10 μm, more preferably from 0.5 to 5 μm. A thickness of the second layer which is too great would spoil the irregularity of the surface of a permanent support and increase the gloss of the support unnecessarily, thus reducing the print approximation. On the other hand, the second layer being too thin would result in damage of the layer. When two or more image receiving layers are transferred to a permanent support, it is preferable to keep the total thickness within the above range.

According to the image receiving sheet of the present invention, the 2-diazo-1,2-quinone compound of the present invention is added to at least one of the first and second image receiving layers. In view of the thickness of the image receiving layers, it is preferred that the compound is added to the second image receiving layer. The compound may be added to the corresponding layer in an amount of from 0.01 to 60% by weight, preferably from 1 to 20% by weight, on a solid basis. If the amount of the compound is smaller than 0.01% by weight, an insufficient decrease in the inter-layer adhesion strength would result. If the amount is larger than 60% by weight, the formation of an image having poor qualities would result due to the effect of nitrogen gas generated after exposure to light, although the decrease in the inter-layer adhesion strength would be sufficient.

The above image receiving sheet may be incorporated into the image forming material system for use, according to U.S. Pat. No. 4,766,053.

Image forming techniques as described in U.S. Pat. No. 4,766,053 may be applied to a process for the formation of a transferable image in which the image receiving sheet of the present invention is used, but it may be most preferable to use a support on which a delamination layer is superposed. Without a delamination layer, an image portion itself must be transferred directly to a permanent support. In such an instance, according to various experiments, there are a limited number of suitable materials, and it is necessary to increase the thermal transfer temperature. In contrast, the use of a delamination layer is advantageous in that separation of functions becomes possible, temperature latitude increases, and a wide variety of permanent support materials can be used. The delamination layer can be provided according to process described, for example, in U.S. Pat. No. 4,482,625. Additional materials used for the delamination layer include vinyl acetate copolymers, vinyl chloride copolymers, polyvinylidene chlorides, vinylidene chloride copolymers, ethylene copolymers such as ethylene/vinyl acetate, ethylene/ester acrylate, ethylene/vinyl chloride and ethylene/acrylate, polyvinyl acetal such as polyvinyl butyral and polyvinyl formal, rubbers such as rubber chloride and synthetic rubber, and polyolefines such as polyethylene and polypropylene, etc. The delamination layer may have a thickness of 0.1 to 10 μm. When a photographic image is developed, the delamination layer under the non-image portion may be subjected to etching, leaving only the part of the layer under the image portion, or a color image may be formed on the entire delamination layer without etching.

To make use of the capacity of the compound of the present invention to change its polarity, the compound can be applied effectively to image forming materials such as a photoresist, a print board, and the like, according to the aforementioned references which disclose recording materials using an optical rearrangement reaction, in which the development of images is carried out using a developer such as an alkali solution or the like. In such a case, excellent results, e.g., increase in developer-resistance in the unexposed portion, may also be obtained because of the ability of the 2-diazo-1,2-quinone compound of the present invention to localize itself easily on the surface of an image receiving layer. These results cannot be obtained by the use of any 2-diazo-1,2-quinone compound that has no alkyl group substituted by fluorine atoms.

For the purpose of ensuring delamination between the layers desired, a treatment for increasing adhesion strength can be conducted so as to prevent delamination between the compound-containing layer and the adjoining layer opposite to the layer desired to be separated therefrom (e.g., addition of adhesion accelerator and undercoating of base).

Examples of the present invention are given below by way of illustration and not by way of limitation. All parts, percents, ratios and the like are by weight unless indicated otherwise.

EXAMPLE 1

[synthesis of 4-(1H,1H,2H,2H-heptadecafluorodecyloxy)-sulfonyl-2-diazo-1,2-naphthoquinone]

A mixture consisting of 13.4 g of 2-diazo-1,2-naphthoquinone-4-sulfonyl chloride, 23.2 g of 1H,1H,2H,2H-heptadecafluorodecanol, and 100 ml of acetonitrile was stirred. To this mixture, 20 ml of acetonitrile containing 5.16 g of triethylamine was added dropwise. After completion of the dropwise addition, the resulting reaction mixture was added dropwise to ice-cold water.

The thus formed product was extracted with ethyl acetate, and the extract was dried with anhydrous magnesium sulfate to remove the solvent. Thereafter, the crude product thus obtained was subjected to column chromatography to isolate 15.6 g of purified 4-(1H,1H,2H,2H-heptadecafluorodecyloxy)sulfonyl-2-diazo-1,2-naphthoquinone having a melting point (decomposition point) of 125° to 127° C.

EXAMPLE 2

[synthesis of 5-(1H,1H,2H,2H-heptadecafluorodecyloxy)sulfonyl-2-diazo-1,2-naphthoquinone]

A mixture consisting of 13.4 g of 2-diazo-1,2-naphthoquinone-5-sulfonyl chloride, 23.2 g of 1H,1H,2H,2H-heptadecafluorodecanol, and 100 ml of tetrahydrofuran was stirred. To this mixture 20 ml of tetrahydrofuran containing 5.16 g of triethylamine was added dropwise. After completion of the dropwise addition, the resulting reaction mixture was added dropwise to ice-cold water to obtain a precipitate.

The thus formed product was collected by filtration and washed with water to obtain a crude product. Thereafter, the crude product thus obtained was subject to recrystallization using an acetone/methanol solvent system to isolate 21.6 g of purified 5-(1H,1H,2H,2H-heptadecafluorodecyloxy)sulfonyl-2-diazo-1,2-naphthoquinone having a melting point (decomposition point) of 127° to 129° C.

EXAMPLE 3

[synthesis of 4-(4-(1H,1H,2H,2H-heptadecafluorodecyl)thio)-phenoxysulfonyl- 2-diazo-1,2-naphthoquinone]

1) Synthesis of (4-(1H,1H,2H,2H-heptadecafluorodecyl)thio)phenol

A mixture consisting of 12.6 g of p-thiohydroquinone and 180 ml of dimethylacetamide was stirred at −20° C. To this mixture, 19.3 g of sodium methoxide dissolved in 28% methanol solution and then 57.4 g of 1H,1H,2H,2H-heptadecafluorodecyl iodide dissolved in dimethylacetamide were added, in that order. When the disappearance of the starting materials was confirmed by means of thin layer chromatography, the reaction mixture was added to water, and the crude product thus formed was isolated by extracting it with ethyl acetate and drying the extract to remove the solvents. Thereafter, the phenol compound thus isolated was purified by means of column chromatography.

2) Synthesis of 4-(4-(1H,1H,2H,2H-heptadecafluorodecyl)thio)phenoxysulfonyl-2 -diazo-1,2-naphthoquinone A mixture consisting of 5.37 g of 2-diazo-1,2-naphthoquinone-4-sulfonyl chloride, 11.5 g of the just obtained (4-(1H,1H,2H,2H-heptadecafluorodecyl)thio)phenol, and 50 ml of acetonitrile was stirred on an ice bath. To this mixture, 10 ml of acetonitrile containing 2.12 g of triethylamine was added dropwise. After completion of the dropwise addition, the resulting reaction mixture was added dropwise to ice-cold water to obtain a precipitate. The thus formed precipitate was collected by filtration and washed with water to obtain a crude product. Thereafter, the crude product thus obtained was subjected to recrystallization using an acetone/methanol solvent system to isolate 13.3 g of purified 4-(4-(1H,1H,2H,2 H-heptadecafluorodecyl)thio)phenoxysulfonyl-2-diazo-1,2-naphthoquinone having a melting point (decomposition point) of 121° to 123° C.

EXAMPLE 4

[synthesis of 5-(4-(1H,1H,2H,2H-heptadecafluorodecyl)thio)-phenoxysulfonyl- 2-diazo-1,2-naphthoquinone]

This compound was prepared from 5.37 g of 2-diazo-1,2-naphthoquinone-5-sulfonyl chloride and 11.5 g of the (4-(1H,1H,2H,2H-heptadecafluorodecyl)thio)phenol synthesized in Example 3, part 1), in a manner similar to that in Example 3. In this way, 14.5 g of the purified compound having a melting point (decomposition point) of 138° to 140° C. was obtained.

EXAMPLE 5

[synthesis of 4-(4-(1H,1H,2H,2H-heptadecafluorodecyloxy)-carbonyl)phenoxysulfonyl- 2-diazo-1,2-naphthoquinone]

1) Synthesis of 4-(1H,1H,2H,2H-heptadecafluorodecyloxy)carbonyl)phenol

A mixture consisting of 5.52 g of 4-hydroxybenzoic acid, 18.6 g of 1H,1H,2H,2H-heptadecafluorodecanol and 0.7 ml of concentrated sulfuric acid and 150 ml of toluene was subjected to heating reflux. After 5 hours of the reflux, the reaction mixture was subjected to extraction with ethyl acetate, and the extract was dried with anhydrous magnesium sulfate to remove the solvents. In this manner, 8.93 g of the intended compound was obtained.

2) Synthesis of 4-(4-(1H,1H,2H,2H-heptadecafluorodecyloxy)carbonyl)phenoxysulfonyl- 2-diazo-1,2-naphthoquinone A mixture consisting of 1.61 g of 2-diazo-1,2-naphthoquinone-4-sulfonyl chloride, 3.51 g of the just obtained 4-(1H,1H,2H,2H-heptadecafluorodecyloxy)carbonyl)phenol, 30 ml of acetonitrile, and 20 ml of tetrahydrofuran was stirred. To this mixture, 5 ml of acetonitrile containing 0.62 g of triethylamine was added dropwise. After completion of the dropwise addition, the resulting reaction mixture was added dropwise to ice-cold water to obtain a precipitate. The thus formed precipitate was collected by filtration and washed with water to obtain a crude product. The crude product thus obtained was then subjected to recrystallization using an acetone/methanol solvent system to isolate 3.03 g of 4-(4-(1H,1H,2H,2 H-heptadecafluorodecyloxy)carbonyl)phenoxysulfonyl-2-diazo-1,2-naphthoquinone having a melting point (decomposition point) of 148° C.

EXAMPLE 6

[synthesis of
5-(4-(1H,1H,2H,2H-heptadecafluorodecyloxy)-
carbonyl)phenoxysulfonyl-
2-diazo-1,2-naphthoquinone]

This compound was prepared from 2.69 g of 2-diazo-1,2-naphthoquinone-5-sulfonyl chloride and 5.84 g of the (4-(1H,1H,2H,2H-heptadecafluorodecyloxy)carbonyl)phenol synthesized in Example 5, part 1), in a manner similar to that in Example 5. In this way, 3.78 g of the purified compound having a melting point (decomposition point) of 141° to 142° C. was obtained.

EXAMPLE 7

First, a transferable image forming material was prepared according to the following steps.

A delamination solution having the following composition was coated on a polyethylene terephthalate film support (100 μm in thickness) and dried to make the solution into a delamination layer having a thickness of 0.5 μm.

| Coating solution for delamination layer use | |
| --- | --- |
| Alcohol soluble polyamide (CM-8000, manufactured by Toray Industries, Inc.; η(20° C.) in 10 wt % methanol solution, 23 cps) | 7.2 g |
| Polyhydroxystyrene (Resin M, manufactured by Maruzen Oil Co., Ltd.; mean molecular weight, 5500) | 1.8 g |
| Methanol | 400 g |
| Methyl cellosolve | 100 g |

Next, each of the four coating solutions as shown in the following Table 1 (Y, M, C, and B) was applied onto the thus prepared delamination layer and dried to make the solution into a sensitive resin layer having a thickness of 2.4 μm and having a color of yellow (Y), magenta (M), cyan (C) or black (B).

TABLE 1

| Sensitive resin layer solutions | | | | |
| --- | --- | --- | --- | --- |
| | Composition (g) | | | |
| | Y | M | C | B |
| Benzylmethacrylate/methacrylic acid copolymer (molar ratio, 73/27; viscosity η = 0.12)*1 | 60 | 60 | 60 | 60 |
| Pentaerythritol tetraacrylate | 43.2 | 43.2 | 43.2 | 43.2 |
| Michler's ketone | 2.4 | 2.4 | 2.4 | 2.4 |
| 2-(o-chlorophenyl)-4,5-diphenyl imidazole dimer | 2.5 | 2.5 | 2.5 | 2.5 |
| Seika Fast yellow H-0755*2 | 9.4 | — | — | — |
| Seika Fast Carmine 1483*2 | — | 5.2 | — | — |
| Cyanine Blue 4820*2 | — | — | 5.6 | — |
| Mitsubishi Carbon Black MA-100*2 | — | — | — | 6.6 |
| Methyl cellosolve acetate | 560 | 560 | 560 | 560 |
| Methyl ethyl ketone | 280 | 280 | 280 | 280 |

*1: Viscosity (η) as used herein means a limiting viscosity in methyl ethyl ketone solution measured at 25° C.
*2: Manufactured by Dainichiseika Color & Chemicals Mfg Co., Ltd.

Then, a coating solution having the following composition was applied onto each of the thus prepared sensitive resin layers and dried to make the solution into a protective layer having a thickness of 1.5 μm.

| Coating solution for protective layer use | |
| --- | --- |
| Polyvinyl alcohol (GL-05, manufactured by The Nippon Synthetic Chemical Industry) | 60 g |
| Water | 970 g |
| Methanol | 30 g |

In this way, four sensitive transfer sheets (N-P type) coloring sensitive sheets having different colors were obtained, in which a support was superposed with a delamination layer, a sensitive resin layer and a protection layer, in that order.

Each of the thus obtained four sensitive transfer sheets was superposed with a mask using register pins and then exposed to light generated from an ultra-high pressure mercury lamp (2 Kw) at a distance of 50 cm for 15 seconds. Thereafter, the thus exposed transfer sheet was subjected to image development at 35° C. for 15 seconds, 20 seconds, 20 seconds and 10 seconds for yellow image, magenta image, cyan image and black image, respectively, using a developing solution having the following composition to obtain four positive color images on the delamination layer.

| Developing solution | |
| --- | --- |
| $Na_2CO_3$ | 15 g |
| Butyl cellosolve | 1 g |
| Water | 1 l |

Separately from the above steps, an image receiving sheet was prepared as follows. A coating solution having the following composition was applied onto a polyethylene terephthalate film (100 μm in thickness) and dried to make the solution into a first image receiving layer having a thickness of 20 μm.

| Coating solution for use in first image receiving layer | |
| --- | --- |
| Ethylene/vinyl acetate copolymer (Evaflex 10, manufactured by Mitsui Polychemical Co., Ltd.; weight ratio, 81% ethylene/19% vinyl acetate) | 15 g |
| Chlorinated polyethylene (Superclon 07LTA, manufactured by Sanyo-Kokusaku Pulp Co., Ltd.) | 0.075 g |
| Fluorine-based surfactant (Fluorad FC-430, manufactured by 3M) | 0.25 g |
| Toluene | 100 g |

The thus prepared first image receiving layer was further superposed with a second image receiving layer having a thickness of 2 μn by applying and drying a coating solution having the following composition.

| Coating solution for use in second image receiving layer | |
| --- | --- |
| Alcohol soluble nylon (Amilan "CM-8000", manufactured by Toray Industries, Inc.) | 1.5 g |
| Styrene/maleic acid semi-ester copolymer resin (Oxilack SH-101, manufactured by Japan Catalytic Chemical Industry Co., Ltd.) | 1.5 g |
| Pentaerythritol tetraacrylate | 2.1 g |
| Michler's ketone | 0.02 g |

-continued

| Coating solution for use in second image receiving layer | |
|---|---|
| Benzophenone | 0.13 g |
| Methanol | 70 g |
| Methyl cellosolve | 30 g |
| Compound of the present invention* | 0.3 g |

*4-(4-(1H,1H,2H,2H-heptadecafluorodecyl)thio)phenoxysulfonyl-2-diazo-1,2-naphthoquinone Using the thus prepared four positive color images and the image receiving sheet, the following evaluation tests were carried out.

When the image side of a color proofing sheet on which a black image was formed was placed upon the image receiving side of the image receiving sheet using register pins, and the thus prepared pair of sheets was treated with a color art transfer machine (CA-600T, manufactured by Fuji Photo Film Co., Ltd.), the black image was transferred perfectly from the color proofing sheet together with the delamination layer to the image receiving sheet. When color proofing sheets on which cyan, magenta and yellow images were respectively formed were transferred to the thus obtained black image by repeating the above procedure, each color image was transferred perfectly to the image receiving sheet together with each delamination layer, thus resulting in the formation of four color images.

The image side of the image receiving sheet having four transferred color images thus prepared was placed upon a sheet of white art paper and subjected to image transfer in the same manner as the above procedure. Thereafter, the resulting pair of sheets was exposed to light from the base, or support, side of the image receiving sheet using a contact printer equipped with a 1 kw ultra-high mercury lamp (P-607, manufactured by Dainippon Screen Mfg. Co., Ltd.). When the image receiving sheet material was delaminated after 30 seconds of the exposure, the first image receiving layer of the image receiving sheet remained with its support. In other words, the image of interest covered with the second image receiving layer was formed on the permanent support.

The image transferability and peeling strength between the first and second layers of the image receiving sheet are shown in Table 2.

EXAMPLE 8

The process of Example 7 was repeated except that the invention compound 4-(4-(1H,1H,2H,2H-heptadecafluorodecyl)thio)phenoxysulfonyl- 2-diazo-1,2-naphthoquinone used in Example 7 was replaced by another invention compound 4-(1H,1H,2H,2H-heptadecafluorodecyl)oxysulfonyl- 2-diazo-1,2-naphthoquinone.

Image transferability and peeling strength between the first and second layers of the image receiving sheet thus obtained were evaluated in the same manner as in Example 7, with the results shown in Table 2.

EXAMPLE 9

The process of Example 7 was repeated except that the invention compound 4-(4-(1H,1H,2H,2H-heptadecafluorodecyl)thio)phenoxysulfonyl- 2-diazo-1,2-naphthoquinone used in Example 7 was replaced by another invention compound, 4-(1H,1H,2H,2H-heptadecafluorodecyl)oxy)sulfonyl- 2-diazo-1,2-naphthoquinone.

Image transferability and peeling strength between the first and second layers of the image receiving sheet thus obtained were evaluated in the same manner as in Example 7, with the results shown in Table 2.

EXAMPLE 10

The process of Example 7 was repeated except that the invention compound 4-(4-(1H,1H,2H,2H-heptadecafluorodecyl)thio)phenoxysulfonyl- 2-diazo-1,2-naphthoquinone used in Example 7 was replaced by another invention compound, 4-(1H,1H,2H,2H-octafluoropentyl)oxysulfonyl-2-diazo-1,2-naphthoquinone.

Image transferability and peeling strength between the first and second layers of the image receiving sheet thus obtained were evaluated in the same manner as in Example 7, with the results shown in Table 2.

EXAMPLE 11

The process of Example 7 was repeated except that the invention compound 4-(4-(1H,1H,2H,2H-heptadecafluorodecyl)thio)phenoxysulfonyl- 2-diazo-1,2-naphthoquinone used in Example 7 was replaced by another invention compound 4-(1H,1H,2H,2 H-heptadecafluorodecyl)sulfonyl)phenoxysulfonyl- 2-diazo-1,2-naphthoquinone.

Image transferability and peeling strength between the first and second layers of the image receiving sheet thus obtained were evaluated in the same manner as in Example 7, with the results shown in Table 2.

COMPARATIVE EXAMPLE 1

The process of Example 7 was repeated except that the invention compound 4-(4-(1H,1H,2H,2H-heptadecafluorodecyl)thio)phenoxysulfonyl- 2-diazo-1,2-naphthoquinone used in Example 7 was not used in this comparative example.

Image transferability and peeling strength between the first and second layers of the image receiving sheet thus obtained were evaluated in the same manner as in Example 7, with the results shown in Table 2.

TABLE 2

| Compounds added to the second layer | Transferability to art paper | Adhesiveness between the first and second layer (g) | |
|---|---|---|---|
| | | before exposure | after exposure |
| Example 7 (Compound 1) | good | 276 | 11 |
| Example 8 (Compound 2) | good | 220 | 13 |
| Example 9 (Compound 3) | good | 177 | 25 |
| Example 10 (Compound 4) | good | 169 | 46 |
| Example 11 (Compound 5) | good | 230 | 13 |
| Comparative Ex. 1 (no addition) | picking occurred at peeling end | 251 | 275 |

In the above Table, adhesiveness (peeling strength) between the first and second image receiving layers was measured under the following conditions.

1. Image receiving layers, each having an area of 6×16 cm, were prepared as test samples.

2. The moisture of the test samples was adjusted to a constant level by maintaining the samples under a humid atmosphere of 80% RH for 1 hour at 24° C.

3. Mylar tape having a width of 5 cm was applied to the surface of the image receiving layer.

4. Each of the test samples was cut to a width of 4.5 cm.

5. A terminal portion of the image receiving layer was peeled off together with Mylar tape, and the sample was then subjected to inter-layer delamination using a digital force gauge meter (DFG-2K, manufactured by Shimpo Industrial Co., Ltd.) at a delamination speed of 1500 mm/min in order to determine the inter-layer adhesion strength.

As shown in Table 2, in the case of the samples of image receiving layers in which the compound of the present invention was included, adhesiveness between the first and second layers decreased greatly after their exposure to light. As a result, delamination at the time of the transfer of the image layer to the paper support was smooth, thus causing no picking at the peeling end, in contrast to the sample of the comparative example.

EXAMPLE 12

A sensitive solution having the following composition was prepared.

| | |
|---|---|
| 4-(4-(1H,1H,2H,2H-heptadecafluorodecyl)thio)phenoxysulfonyl-2-diazo-1,2-naphthoquinone | 2 g |
| Polyvinyl butyral (Deanka Butyral, manufactured by Denki Kagaku Kogyo K.K.) | 2 g |
| Methyl ethyl ketone | 20 ml |

The thus prepared sensitive solution was coated evenly on an aluminum base board using a whirler and dried to make the solution into a sensitive layer having a thickness of 4 μm. After superposing a positive original, the thus prepared sensitive layer was exposed to light for 100 seconds at a distance of 20 cm from a 100 W high pressure mercury lamp. Thereafter, the resulting layer was placed upon a thermal lamination film and passed through heating rollers which were controlled at a temperature of 125° C. When the laminated film was peeled off from the sensitive layer immediately after the thermal lamination, an excellent positive type relief image comprising the unexposed portion of the sensitive composition layer was found on the aluminum base board, while a negative type relief image comprising the exposed portion of the sensitive layer was found on the delaminated film.

Thus, the present invention provides a 2-diazo-1,2-quinone compound having a substituent group containing an alkyl group which is substituted by a fluorine atom, as well as an image forming material prepared by making use of the compound. The compound of the present invention has a capacity to change its polarity when exposed to light. Because of this capacity, when the invention compound is added to at least one layer of a multi-layer recording material and the layers are exposed to light, the adhesiveness of the compound containing layer to its adjoining layer is reduced effectively compared to the adhesiveness before the light exposure. The compound of the present invention is also applicable to printing plates, resist materials, and the like.

While the present invention has been described in conjunction with specific embodiments thereof, it is evident that many alternatives, modifications and variations will be apparent to those skilled in the art in light of the foregoing description. Accordingly, it is intended to include all such alternatives, modifications and variations as set forth within the spirit and scope of the appended claims.

What is claimed is:

1. A method of improving delamination in an image forming material, wherein said material comprises a base support, at least an image receiving layer provided on said base support, a layer adjacent to the image receiving layer, wherein the layer adjacent is provided between the image receiving layer and the base support, wherein the image receiving layer contains a developed image, and wherein at least the image receiving layer contains a 2-diazo-1,2-naphthoquinone compound, wherein the 4-position of said compound is substituted by a substituent group represented by formula (II):

$$-SO_2-O-R^3 \qquad (II)$$

wherein $R^3$ represents a substituent group containing an alkyl group which has 2 to 20 carbon atoms and is substituted by at least 3 fluorine atoms;

said method comprising:
   a) laminating a permanent support on the image receiving layer containing the developed image; and
   b) delaminating the layer adjacent to the image receiving layer from the image receiving layer after a flood exposure through the base support to transfer the image receiving layer containing the developed image to the permanent support.

* * * * *